(12) United States Patent
Hunt et al.

(10) Patent No.: US 11,266,521 B2
(45) Date of Patent: Mar. 8, 2022

(54) OSTOMY ATTACHMENT

(71) Applicant: UNIVERSITY OF LIMERICK, Limerick (IE)

(72) Inventors: Rhona Hunt, Roscommon Town (IE); Kevin Kelleher, Dublin (IE); Leonard O'Sullivan, Clonlara (IE)

(73) Assignee: University of Limerick, Limerick (IE)

( * ) Notice: Subject to any disclaimer, the term of this patent is extended or adjusted under 35 U.S.C. 154(b) by 767 days.

(21) Appl. No.: 16/088,810

(22) PCT Filed: Mar. 16, 2017

(86) PCT No.: PCT/EP2017/056259
§ 371 (c)(1),
(2) Date: Sep. 26, 2018

(87) PCT Pub. No.: WO2017/167582
PCT Pub. Date: Oct. 5, 2017

(65) Prior Publication Data
US 2020/0297524 A1    Sep. 24, 2020

(30) Foreign Application Priority Data
Mar. 31, 2016   (GB) ..................................... 1605516

(51) Int. Cl.
A61F 5/44    (2006.01)
A61F 5/443   (2006.01)
A61F 5/448   (2006.01)

(52) U.S. Cl.
CPC ............ *A61F 5/4405* (2013.01); *A61F 5/443* (2013.01); *A61F 5/448* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 2,563,597 | A | * | 8/1951 | Friedman et al. ...... | A61F 5/445 604/339 |
| 2,604,096 | A | * | 7/1952 | Smith ..................... | A61F 5/445 604/334 |
| 2,652,055 | A | * | 9/1953 | Baron ..................... | A61F 5/445 604/334 |
| 4,238,059 | A | * | 12/1980 | Caraway ................ | A61F 5/4405 222/529 |
| 4,867,749 | A | * | 9/1989 | Steer ....................... | A61F 5/448 604/337 |

(Continued)

FOREIGN PATENT DOCUMENTS

JP           45-1800           1/1970

*Primary Examiner* — Guy K Townsend
(74) *Attorney, Agent, or Firm* — Perkins Coie LLP (57) ABSTRACT

An ostomy attachment comprises a flexible annular seal configured to embrace a stoma and a spout that in use is disposed beneath the stoma and configured to collect ostomy output at skin level and direct ostomy output away from the patient and annular seal and into an ostomy bag, in which the flexible annular seal is formed from an absorbent material and the spout is formed from a non-absorbent material. The annular seal may be an open ring comprising at least one mouldable arm that in use can be wrapped at least partially around the patients' stoma.

16 Claims, 8 Drawing Sheets

(56) References Cited

U.S. PATENT DOCUMENTS

| | | | | |
|---|---|---|---|---|
| 4,988,343 A * | 1/1991 | Ballan | ............... | A61F 5/4407 |
| | | | | 383/66 |
| 5,135,199 A * | 8/1992 | Cross | ............... | A61F 5/4407 |
| | | | | 251/319 |
| 5,429,626 A * | 7/1995 | Fenton | ............... | A61F 5/448 |
| | | | | 604/339 |
| 5,935,115 A * | 8/1999 | Espina | ............... | A61F 5/445 |
| | | | | 604/277 |
| 6,312,415 B1 * | 11/2001 | Nielsen | ............... | A61F 5/443 |
| | | | | 604/327 |
| 2003/0004477 A1 * | 1/2003 | Nielsen | ............... | A61F 5/448 |
| | | | | 604/336 |
| 2003/0229324 A1 * | 12/2003 | King | ............... | A61M 3/0287 |
| | | | | 604/339 |
| 2004/0111072 A1 * | 6/2004 | McKissick | ............... | A61F 5/445 |
| | | | | 604/332 |
| 2008/0060679 A1 * | 3/2008 | Rosenberg | ............... | B08B 3/04 |
| | | | | 134/22.1 |
| 2008/0262446 A1 * | 10/2008 | Ryder | ............... | A61F 5/445 |
| | | | | 604/317 |
| 2010/0174253 A1 * | 7/2010 | Cline | ............... | A61F 5/445 |
| | | | | 604/328 |
| 2014/0236111 A1 * | 8/2014 | Casado | ............... | A61F 5/44 |
| | | | | 604/332 |
| 2015/0223966 A1 * | 8/2015 | Mahood | ............... | A61F 5/4407 |
| | | | | 604/337 |
| 2017/0140103 A1 * | 5/2017 | Angelides | ............... | G16H 80/00 |
| 2019/0247050 A1 * | 8/2019 | Goldsmith | ............... | A61B 17/00491 |
| | | | | 604/334 |
| 2021/0205117 A1 * | 7/2021 | Spain | ............... | A61F 5/443 |
| | | | | 604/334 |
| 2021/0212856 A1 * | 7/2021 | Kelleher | ............... | A61F 5/448 |
| | | | | 604/334 |

* cited by examiner

OSTOMY ATTACHMENT

This application is a National Stage of International Application PCT/EP2017/056259, filed Mar. 16, 2017, under PCT Article 21(2) in English; which claims the priority of Great Britain Application No. 1605516.2, filed Mar. 31, 2016. The contents of the above-identified applications are incorporated herein by reference in their entireties.

BACKGROUND TO THE INVENTION

The terms ostomy and stoma are general descriptive terms that are often used interchangeably though they have different meanings. An ostomy refers to the surgically created opening in the body for the discharge of body wastes. A stoma is the actual end of the small or large bowel or ureter that can be seen flush with or protruding through the abdominal wall. The most common specific types of ostomies are: colostomy, where a portion of the colon or rectum is removed and the remaining colon is brought to the abdominal wall and generally protrudes through the abdominal wall to form a stoma; ileostomy, where a surgically created opening in the small intestine, at the end of the remaining ileum, is brought through the abdominal wall to form a stoma; and a urostomy, where a section of the small bowel is surgically removed and relocated as a passageway for urine to pass from the kidneys to the outside of the body through a stoma.

A patient with an ostomy can get chemical dermatitis when the output from the stoma comes into contact with the skin around the stoma. This can happen either because there is an area of the skin around the stoma exposed to stoma output (not protected by an ostomy device) or because the material that is used to protect the skin starts to absorb the stoma output, resulting in breakdown of the material and contact of the output with the skin. The most problematic cases are stomas that are not protruding sufficiently, retracted stomas and stomas that are asymmetric in shape to include loop and end stomas. This can be categorised as stomas that are emptying onto the skin. The requirement to cut a hole in an ostomy bag to exact the shape and size the patients' stoma creates deficiencies in obtaining an optimum seal. There are ostomy seals on the market, used to protect the skin around the stoma from stoma output, but these are generally hydrocolloid materials which are absorbent, and thus, even if they seal/wrap around the stoma fully, they can absorb the output from the stoma, and therefore damage the skin.

A further problem with known ostomy attachments is "pancaking", which occurs when ostomy output sits on or around the stoma and fails to drop into the ostomy bag, causing the ostomy bag to flatten and close, and subsequent ostomy output to push its way under the flange of the bag, causing chemical dermatitis, unpleasant odour and leaks.

EP0197672 describes a urostomy appliance in a two-part form, namely a first parts comprising a hydrocolloid adhesive pad that attached to the skin and having a central hole for receipt of a stoma (in which the hole is cut by a patient prior to application of the pad), and a fitting for the pad having a dome which, upon fitting, sits over the stoma, and an outlet pipe that is spaced outwardly from the skin. The device has a number of problems: first, the outlet pipe 34 is spaced from the skin leaving a void area which can be seen in FIG. 2 where ostomy output can collect and pool; secondly, the dome has a predefined shape having a diameter that is generally greater than the diameter of the hole cut in the adhesive pad, meaning that ostomy output will necessarily come into contact with the hydrocolloid adhesive pad, resulting in chemical breakdown of the hydrocolloid and contact between the ostomy output and the users skin; and thirdly, use of the device requires that a user cut a hole in the adhesive pad corresponding to the shape of their stoma.

It is an object of the invention to overcome at least one of the above-referenced problems.

STATEMENTS OF INVENTION

The invention provides an ostomy attachment comprising an annular seal configured to embrace a stoma and a spout that in use is disposed beneath the stoma and configured to collect ostomy output at skin level and direct the collected output away from the patient and annular seal and directly into the ostomy bag. The seal and rim of the spout are flexible to facilitate forming a seal around different sized and shaped stoma (for example, the annular seal can be formed from a hydrocolloid material), and the spout is formed from non-absorbent material (for example a thermoplastic polymer). The annular seal ensures that the attachment conforms closely to the periphery of the stoma, and the spout ensures that ostomy output is directed away from the patient and the annular seal. This helps avoid the mouldable seal material coming into contact with the ostomy output and being degraded. In addition, the spout reduces the risk of ostomy output in the ostomy bag splashing back onto the area around the stoma, and helps avoid or minimise the problem of "pancaking" and ensures that the bag remains open, even when the patient is lying down. The non-absorbent spout also provides a surface for the user to interact with, which allows less handling of the absorbent annular seal.

In a first aspect, the invention provides an ostomy attachment comprising an annular seal configured to embrace a stoma and a spout that in use is disposed beneath the stoma and configured to direct ostomy output away from the patient and annular seal and into the ostomy bag. The invention also provides an ostomy attachment kit for assembling an ostomy attachment of the invention, the kit comprising a plurality of annular seals, each configured to embrace a stoma, and at least one spout configured for attachment to an internal rim of the seal and configured to direct ostomy output away from the patient and annular seal and into the ostomy bag during use.

In one embodiment, the annular seal is flexible. In one embodiment, the annular seal comprises (or is formed from) a mouldable material. In one embodiment, the annular seal comprises (or is formed from) an absorbent material. In one embodiment, the annular seal comprises (or is formed from) a hydrocolloid material. The use of a flexible seal avoids the need for the user to cut a hole in an adhesive pad, as required in EP0197672, and allows simple and accurate adjustability of the seal around the stoma. In addition, it allows for size adjustment during post-surgical edema reduction, or other sizing or shape changes that occur, resulting in a more secure seal.

In one embodiment, the spout comprises (or is formed from) a non-absorbent material. Examples of non-absorbent materials include silicone, polyurethane, or thermoplastic polymers. In one embodiment, the non-absorbent material is non-absorbent to ostomy output, in particular fecal matter. In one embodiment, the spout is flexible, in particular sufficiently flexible to allow it to be deformed by the bag so that the spout does not prevent the bag being attached to the annular seal.

In one embodiment, the spout is a low-profile spout. This means that the spout generally does not protrude more than 6 mm.

In one embodiment, the spout comprises a partially annular inner rim portion configured to engage with a rim portion of the annular seal, in which the partially annular inner rim portion of the spout is flexible to allow it to conform to a non-uniform stoma.

In one embodiment, the partially annular inner rim of the spout is thin and optionally angled to optimise collection of ostomy output and delivery of ostomy output directly into an ostomy bag.

In one embodiment, the annular seal is a complete ring, and resiliently deformable to enable the ring to conform to different sized and shaped stomas.

In another embodiment, the annular ring is an open ring having an upper part comprising at least one, preferably two, arms configured for in-situ moulding around a patients' stoma, and a lower part comprising the spout.

In one embodiment, the spout comprises an at least partially annular ring configured for engagement with the internal rim of the annular seal.

In one embodiment, an underside of the spout comprises a partially annular slot configured for sealing engagement with part of the ostomy bag, preferably a rim of an ostomy bag aperture.

In one embodiment, the spout is detachably attached to the annular seal. This allows the ostomy attachment to be provided in a modular format, where a user can choose from a plurality of annular seals, for example to pick a seal formed from a hydrocolloid material that suits the user's skin. It also allows a user choose from a plurality of different spouts.

The invention also provides an ostomy bag kit comprising an ostomy bag and an ostomy attachment according to the invention.

The invention also provides a method for attaching an ostomy bag to a patient with a stoma, which method employs an ostomy bag having an aperture for receipt of ostomy output, and an ostomy attachment according to the invention. Typically, the method comprises placing the ostomy attachment on the patient such that the annular seal at least partially and ideally fully surrounds the patients' stoma and the spout is disposed below the patients' stoma, and preferably attaching the ostomy bag to the ostomy attachment and/or patient such that the spout projects into the aperture of the bag.

In one embodiment, the annular seal is an open ring in which the open ring comprises at least one mouldable arm that in use can be wrapped at least partially around the patients' stoma. Typically, the method comprises the additional step of moulding the at least one mouldable arm around at least part of the patients' stoma.

In one embodiment, the annular skin abutting plate has an upper part comprising two mouldable arms configured for in-situ adjustment to fully embrace the patients' stoma. The method typically comprises the additional step of moulding the two mouldable arms around the patients' stoma.

In one embodiment, an underside of the spout comprises a partially annular slot configured for engagement with part of the bag, typically part of a rim of the aperture of the ostomy bag, in which the step of attaching the bag to the ostomy attachment typically includes a step of engaging the rim of the aperture of the bag with the slot on the underside of the spout.

Hydrocolloid materials are typically used against the skin to secure ostomy bags around stomas. This material can, upon removal, peel off layers of skin, causing skin complications in people with stomas. Hydrocolloids can take some time to adhere correctly to the skin—they have to be warmed up and held to the skin for some time before sticking securely. Ostomy devices are typically disposable, single-use devices. As such, patients can run up quite a large bill when repeatedly replacing devices.

Accordingly, in a further aspect, the invention provides a modular two-part fixing plate comprising a reusable outer ring and a disposable inner ring having an aperture, and in which the inner and outer rings are configured for removable engagement. In one embodiment, the outer ring comprises a hypoallergenic skin-safe adhesive. In one embodiment, the inner ring comprises a mouldable, preferably absorbent, material.

The fixing plate is primarily intended for attaching an ostomy bag. However, other applications may include use as a wound dressing (where the inner ring is replaced regularly), or as a means of managing fistulas or attaching fistula bags to fistulas.

In particular, the modular two-part fixing plate comprises: a reusable outer ring having a skin-abutting side comprising a hypoallergenic skin-safe adhesive and a protecting layer on the outer side. The non-reusable inner ring is configured for removable engagement within the outer ring and typically comprises an annulus formed of a mouldable, preferably absorbent, material with a central aperture configured in one embodiment to embrace a stoma during use and optionally a peripheral annular housing configured to support the mouldable absorbent annulus and in one embodiment provide a landing site for an ostomy bag.

In one embodiment, the hypoallergenic skin-safe adhesive is silicone adhesive. In one embodiment, the mouldable absorbent material is a mouldable hydrocolloid material.

In one embodiment, the inner circumference of the outer ring and the outer circumference of the inner ring comprise complimentary formations configured for removable inter-engagement between the outer and inner rings. In one embodiment, the formations are shoulders configured for inter-engagement. Other types of formations suitable for providing removable inter-engagement between the inner and outer rings are possible and will be apparent to a person skilled in the art.

In one embodiment, the outer and inner rings are configured such that when assembled the skin-abutting side of the inner ring is substantially flush with the skin abutting side of the hydrocolloid annulus.

In one embodiment, the outer and inner rings are configured such that when assembled the outer protecting layer of the outer ring is substantially flush with the landing site for the ostomy bag.

In one embodiment, the support housing is an annular layer of material that is disposed on top of the hydrocolloid annulus and includes a circumferential flange that extends beyond the external periphery of the hydrocolloid annulus.

In one embodiment, the outer surface of the peripheral annular housing comprises a polymer material suitable for engagement with a stoma bag. Examples of suitable material include polyurethane and thermoplastic elastomer.

In one embodiment, an inner circumference of the outer ring comprises a material that is harder than the hypoallergenic skin-safe adhesive. This may be a hardened polymer such as polyurethane or thermoplastic elastomer or cured silicone. The purpose of the hardened inner circumference is to give structure to the inner ring.

In one embodiment, the non-reusable inner ring comprises a peripheral tab to facilitate separation of the inner ring from the outer ring.

In one embodiment, the reusable outer ring comprises a peripheral tab to facilitate separation of the outer ring from the users' skin. In one embodiment, the outer ring comprises two peripheral tabs, typically disposed on diametrically opposite sides of the outer ring.

The invention also provides an ostomy bag kit comprising a plurality of ostomy bags, a plurality of non-reusable inner rings, and at least one reusable outer ring.

The invention also provides a method of using a modular two-part fixing plate according to the invention comprising the steps of attaching the modular two-part fixing plate to a users' skin such that the central aperture of the annulus embraces the users' stoma, attaching an ostomy bag to the peripheral annular housing of the inner ring of the two-part fixing plate, using the ostomy bag for a period of time, removing the inner ring and ostomy bag together leaving the reusable outer ring in-situ, attaching a replacement inner ring to the outer ring such that the central aperture of the hydrocolloid annulus embraces the users' stoma, and attaching a replacement ostomy bag to the peripheral annular housing of the inner ring.

Figure 9:
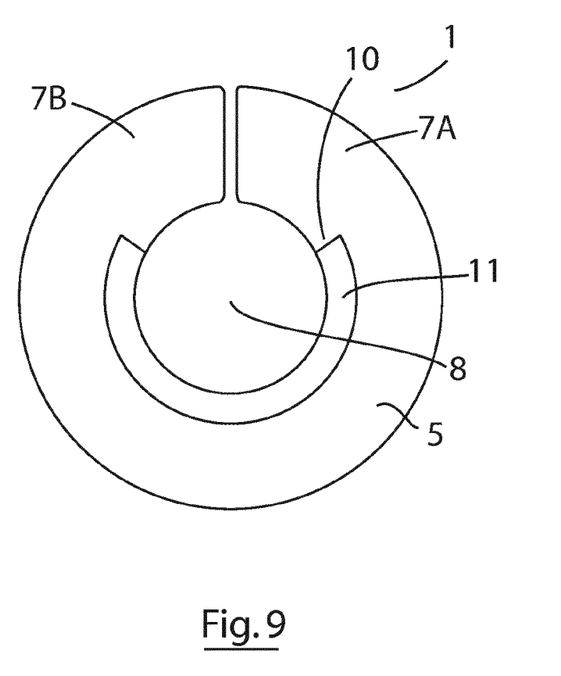
FIG. 9 is a top plan view of an ostomy attachment according to an alternative embodiment of the invention.
Figure 10:
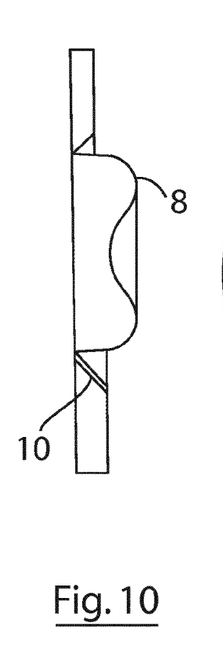
FIG. 10 is a side elevational view of the ostomy attachment of FIG. 9.

In another aspect, the invention provides an ostomy attachment comprising an absorbent annular seal configured to embrace a stoma and an at least partially annular rim portion that is disposed along at least a portion of an internal rim of the annular seal that in use is disposed beneath the stoma and configured to direct ostomy output away from the patient. This embodiment is suitable for use with convex users with limited bag aperture size expansion. An embodiment of an ostomy attachment according to this aspect of the invention is illustrated in FIGS. 9 and 10.

In one embodiment, the annular seal is flexible. In one embodiment, the annular seal comprises (or is formed from) a mouldable material. In one embodiment, the annular seal comprises (or is formed from) an absorbent material. In one embodiment, the annular seal comprises (or is formed from) a hydrocolloid material.

In one embodiment, the at least partially annular rim portion comprises (or is formed from) a non-absorbent material. Examples of non-absorbent materials include silicone, polyurethane, or thermoplastic polymers.

In one embodiment, the at least the partially annular inner rim portion of the spout is flexible to allow it to conform to a non-uniform stoma.

In one embodiment, the at least partially annular rim portion is thin and optionally angled to optimise collection of ostomy output and delivery of ostomy output directly into an ostomy bag.

In one embodiment, the annular seal is a complete ring, and resiliently deformable to enable the ring to conform to different sized and shaped stomas.

In another embodiment, the annular ring is an open ring having an upper part comprising at least one, preferably two, arms configured for in-situ moulding around a patients' stoma.

In one embodiment, the at least partially annular rim portion comprises an at least partially annular ring configured for engagement with the internal rim of the annular seal.

In one embodiment, an underside of the spout comprises a partially annular slot configured for sealing engagement with part of the ostomy bag, preferably a rim of an ostomy bag aperture.

In one embodiment, the at least partially annular rim portion is detachably attached to the annular seal. This allows the ostomy attachment to be provided in a modular format, where a user can choose from a plurality of annular seals, for example to pick a seal formed from a hydrocolloid material that suits the user's skin. It also allows a user choose from a plurality of different rim portions.

The invention also provides an ostomy bag kit comprising an ostomy bag and an ostomy attachment according to the invention.

Other aspects and preferred embodiments of the invention are defined and described in the other claims set out below.

BRIEF DESCRIPTION OF THE FIGURES

FIG. 15A is a bottom plan view and 15B is a perspective view from below of the modular two-part fixing plate of the invention showing the inner ring of FIG. 13 concentrically engaged within the outer ring of FIG. 11;

FIG. 16A is a top plan view and 16B is a perspective view from above of the modular two-part fixing plate of the invention showing the inner ring of FIG. 13 concentrically engaged within the outer ring of FIG. 11;

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

The term "modular" as used herein means that the plate is formed from two parts which can attach together and separate as required. This facilitates the plate being formed with a reusable part (outer ring) formed of a material suitable for attaching to the skin, and a second disposable part (inner ring) formed from a hydrocolloid absorbent material suitable for shaping to conform to the stoma. The inner ring is typically adapted for engagement with an ostomy bag, thus allowing the bag and inner ring to be removed together. The modular nature of the fixing plate allows a user to fix the reusable outer ring securely in position, and leave it in situ while allowing multiple changes of the inner ring and ostomy bag. This facilitates ease of use for the user, provides security insofar as the outer ring once in situ does not have to be removed every time the bag is changed, and avoids mechanical dermatitis problems associated with repeated removal of hydrocolloid fixing plates. In addition, use of silicone (or another hypoallergenic skin-safe adhesive) ensures immediate adhesion to the skin, providing the users with a greater sense of security.

The "protecting layer" as referenced above is a material that provides for handling of the hypoallergenic skin-safe adhesive, and also provides a landing site for the securing the inner ring. In one embodiment, the protecting later is a fabric or polymer film that ideally the adhesive cures to, for example a polyurethane film or a polyester fabric.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings and initially to FIGS. 1 to 4, there is shown an ostomy attachment according to the invention and indicated generally by the reference numerals 1. The attachment 1 comprises an annular seal 4 and a spout 2 formed of a non-absorbent material which is configured to direct ostomy output away from the annular seal and the users' skin. In more detail, the annular seal 4 in the form of an open ring and having a lower part 5 that is attached to the spout 2 and an upper part formed into two mouldable arms 7A, 7B that can be adjusted to embrace the stoma 8. The annular seal comprises an absorbent material for example a hydrocolloid material which abuts the skin and has an outer face which presents a landing site for a stoma bag.

Figure 1:
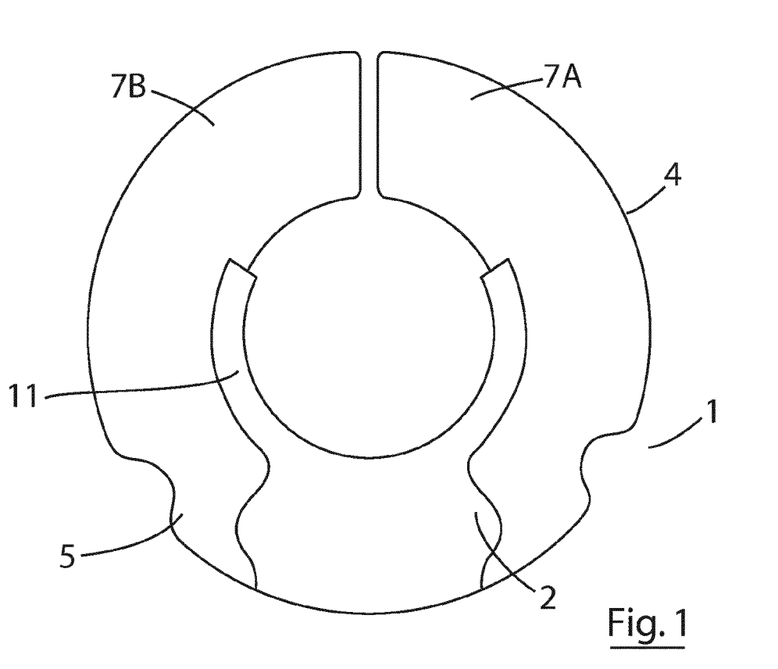
FIG. 1 is a plan view of an ostomy attachment according to the invention.
Figures 2, 3, 4:
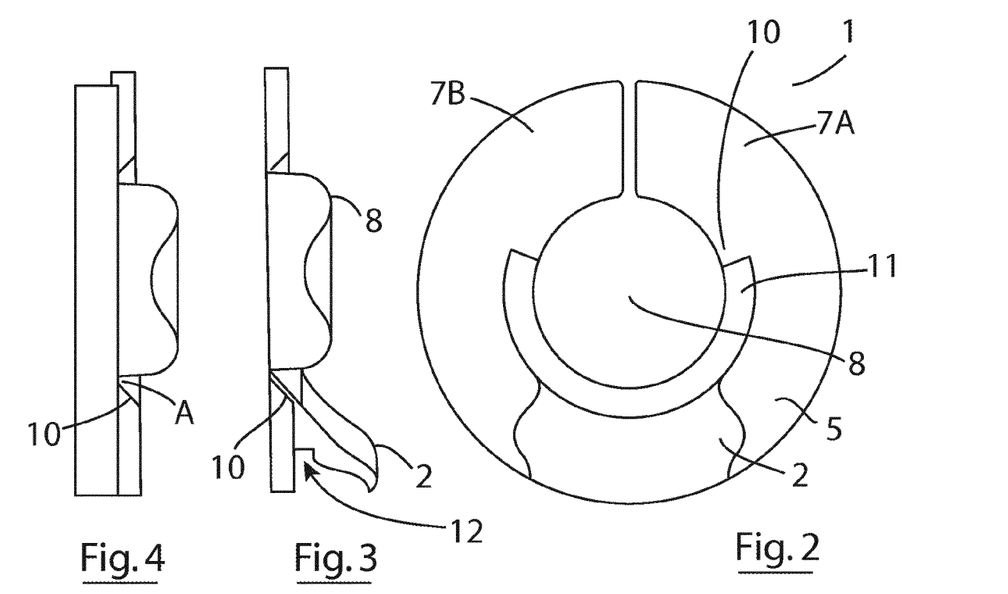
FIG. 2 is a plan view of the ostomy attachment of FIG. 1 attached to a patient and partially embracing a stoma.
FIG. 3 is a sectional side elevational view of the ostomy attachment attached to a patient of FIG. 2.
FIG. 4 is a sectional side elevational view of an ostomy attachment without a spout attached to a patient.

In more detail, and referring to FIGS. 2 to 4, an inner circumference of the annular seal 4 is shaped to form an angled annular shoulder 10, and the spout 2 comprises a part-annular ring 11 that is angled to engage with the shoulder 10, fixing the spout to the annular seal and providing the spout at skin level to optimise collection of ostomy output. In addition, an underside of the spout 2 comprises a curved slot 12 dimensioned to engage with the bag and guide the bag into engagement with the attachment A is best seen in FIG. 3, when the attachment 1 is in-situ on a patient embracing a stoma 8, the spout projects downwardly and outwardly, away from the stoma, thereby directing ostomy output away from the skin and annular seal and into the bag, and also providing an overhang which prevents ostomy output in the bag splashing back against the stoma.

Figure 5:
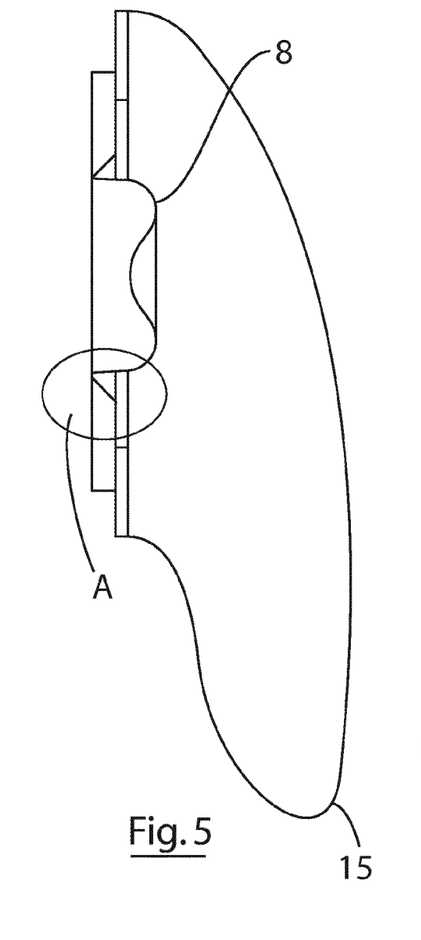
FIG. 5 is a sectional side elevational view of the ostomy attachment of FIG. 4 attached to a patient and an ostomy bag attached to the ostomy attachment, showing where stoma output can come into contact with the patients' skin.

As can be seen in FIGS. 4 and 5, an ostomy attachment without a spout (which are described in the literature) will not prevent splash-back, and will not prevent ostomy output coming into contact with the users' skin at the area marked A. However, even if the seal does initially prevent ostomy output coming into contact with the skin, as these known seals are generally formed of an absorbent hydrocolloid material which is designed to absorb ostomy output, the ostomy output causes the material of the attachment to breakdown, which results in ostomy output coming into contact with the skin. The ostomy attachment of the invention overcomes this problem by providing a spout formed of a non-absorbent material, which is configured to receive output directly from the stoma and direct it away from the skin and the annular seal. Thus, the annular seal is protected from ostomy output, allowing the seal to be formed of an absorbent material, and the spout which is formed on a non-absorbent material does not break down in response to contact with ostomy output.

Figure 6:
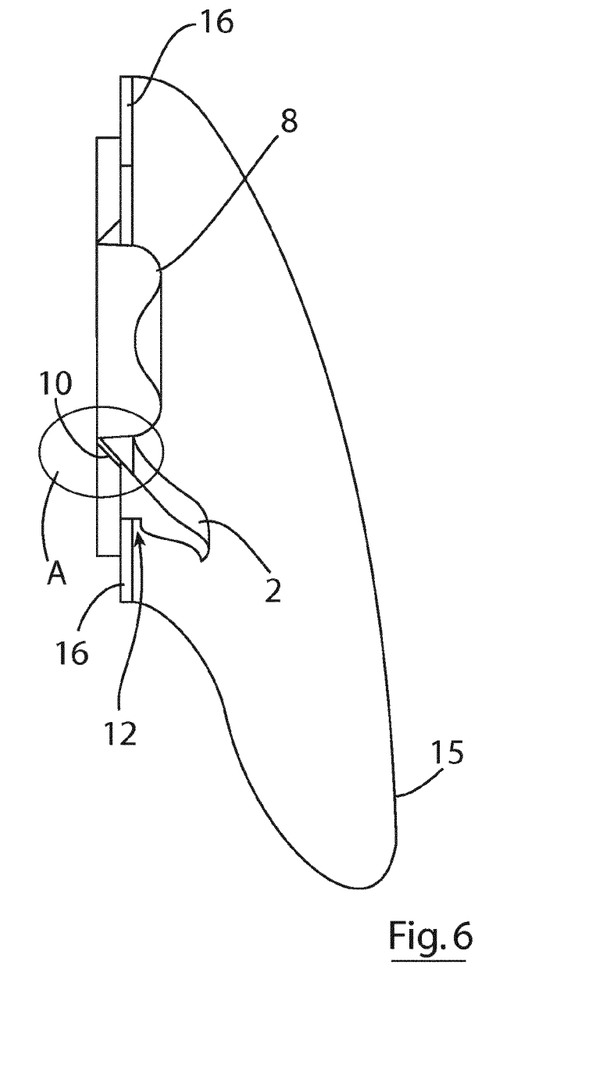
FIG. 6 is a sectional side elevational view of the ostomy attachment of the invention attached to a patient and an ostomy bag attached to the ostomy attachment showing how output from the stoma is directed away from the patients' skin by the spout.

FIG. 6 illustrates an ostomy attachment of the invention 1 attached to a patient and an ostomy bag 15 attached to the ostomy attachment 1 for collection of output from the ostomy bag. The bag 15 has an opening for receipt of ostomy output and an engagement plate 16 formed of a hydrocolloid material forming a periphery around the opening. The engagement plate is configured for engagement with the upper surface of the annular seal 4 and includes a lower part which is dimensioned to engage with the curved slot 12 on the underside of the spout, which helps guide the ostomy bag into engagement with the ostomy attachment.

In use, the attachment 1 is placed against a users' skin partially embracing the users' stoma and with the lower part of the skin abutting plate placed flush against the lower part of the stoma such that the spout is disposed beneath the stoma. The two mouldable arms 7A and 7B are then adjusted such that they conform to the periphery of the stoma, forming a good seal between the ostomy attachment and the stoma. The bag 15 is then attached to the attachment 1 with the lower part of the engagement plate 16 slotting into the curved slot 12. The hydrocolloid material of surface 4 fuses with the hydrocolloid material of the engagement plate, creating a secure attachment.

In the above embodiment, a skin abutting plate having two mouldable arms is described, however it will be appreciated that the plate may instead have one single arm which can be moulded around the upper periphery or the entirety of the stoma. Alternatively, the skin abutting plate may be a closed ring which is dimensioned to fit the users' stoma, or which is adjustable (for example resiliently deformable) to conform to different sized and shaped stomas. In addition, the spout as described above is formed from a non-absorbent, rubber-like material, however it may be formed from other materials, for example other forms of non-absorbent polymer, the details of which will be known to a person skilled in the art.

Examples of absorbent materials for use with the present invention include hydrocolloids, hydrogels and other absorbent materials that may have applications in the wound care and ostomy industry. Examples of non-absorbent materials that may be used with the present invention include polyurethanes, silicones and thermoplastic elastomers.

Figure 7:
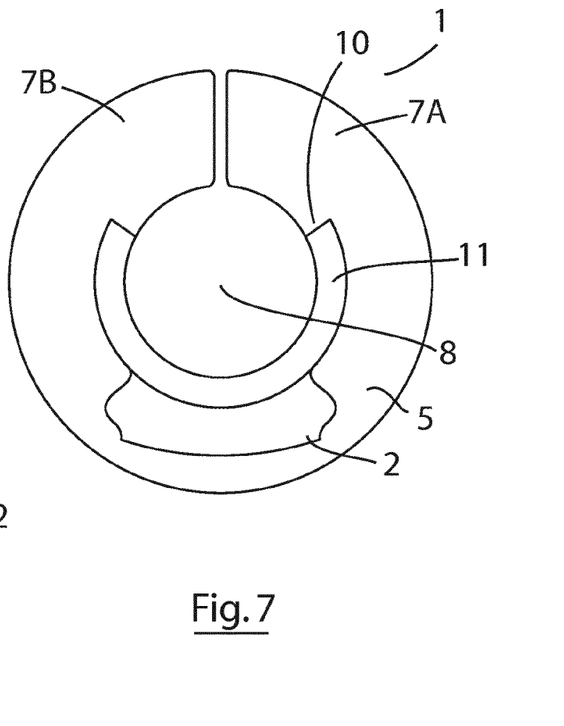
FIG. 7 is a top plan view of an ostomy attachment according to an alternative embodiment of the invention.
Figure 8:
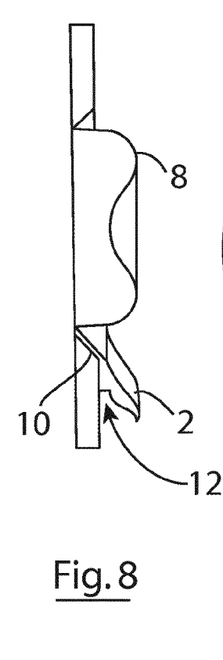
FIG. 8 is a side elevational view of the ostomy attachment of FIG. 7.

Referring to FIGS. 7 and 8, a further embodiment of an ostomy attachment according to invention is illustrated in which parts identified with reference to the previous embodiment are assigned the same reference numerals. In this embodiment, the spout 2 is shorter and has a lower profile than the spout illustrated in the previous embodiment (as illustrated in FIG. 8). In addition, the spout is more flexible that the previous embodiment, and is easily deformable in a direction towards the users' skin. The use of this embodiment is substantially the same as that illustrated with reference to the previous embodiment.

The ostomy attachments described above solve some of the problems of the prior art devices by providing a non-absorbent spout having an inlet at skin level (by virtue of the angled rim), that collects ostomy output at skin level and diverts it away from the users' skin and the annular seal. When the annual seal is an absorbent layer, such as a hydrocolloid, this prevents ostomy output coming into contact with the absorbent material and causing it to break down. In addition, the spout helps direct the ostomy output away from the skin and seal and into the bag, and the underside of the spout helps prevent ostomy output in the bag splashing back on the stoma and/or seal.

Referring to FIGS. 9 and 10, a further embodiment of an ostomy attachment according to invention is illustrated in which parts identified with reference to the previous embodiment are assigned the same reference numerals. In this embodiment, the spout consists of the partially annular rim portion 11 that engages with an internal rim of the seal (as described with reference to the previous embodiment). The use of this embodiment is substantially the same as that illustrated with reference to the previous embodiment.

The ostomy attachment of this embodiment helps with convex bag users where the limitations on size expansion of the bag aperture prevents the use of a large protruding spout.

Referring now to FIGS. 11 to 17, a modular two-part fixing plate for an ostomy bag will be described. The fixing plate, which is indicated generally by the reference numeral 20, comprises two parts, namely an outer ring 21 which is reusable (i.e. can be used multiple times and does not have to be replaced when an ostomy bag is replaced) and an inner ring 22 which is non-reusable (i.e. it is generally discarded when an ostomy bag is discarded).

Figure 11:
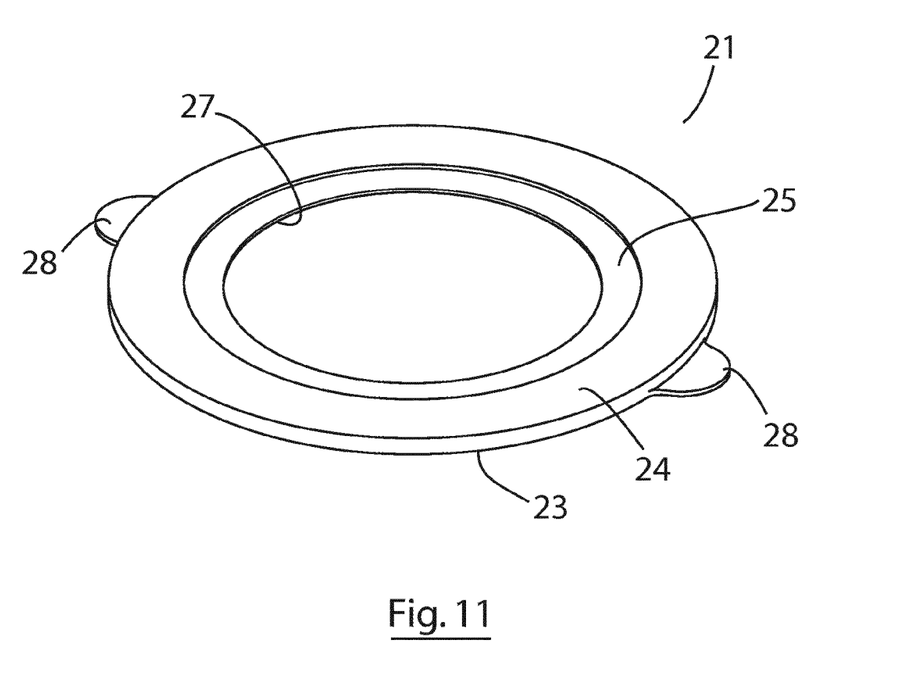
FIG. 11 is a perspective view of a reusable outer ring forming a first part of the modular two-part fixing plate of the invention.
Figures 12A, 12B, 13:
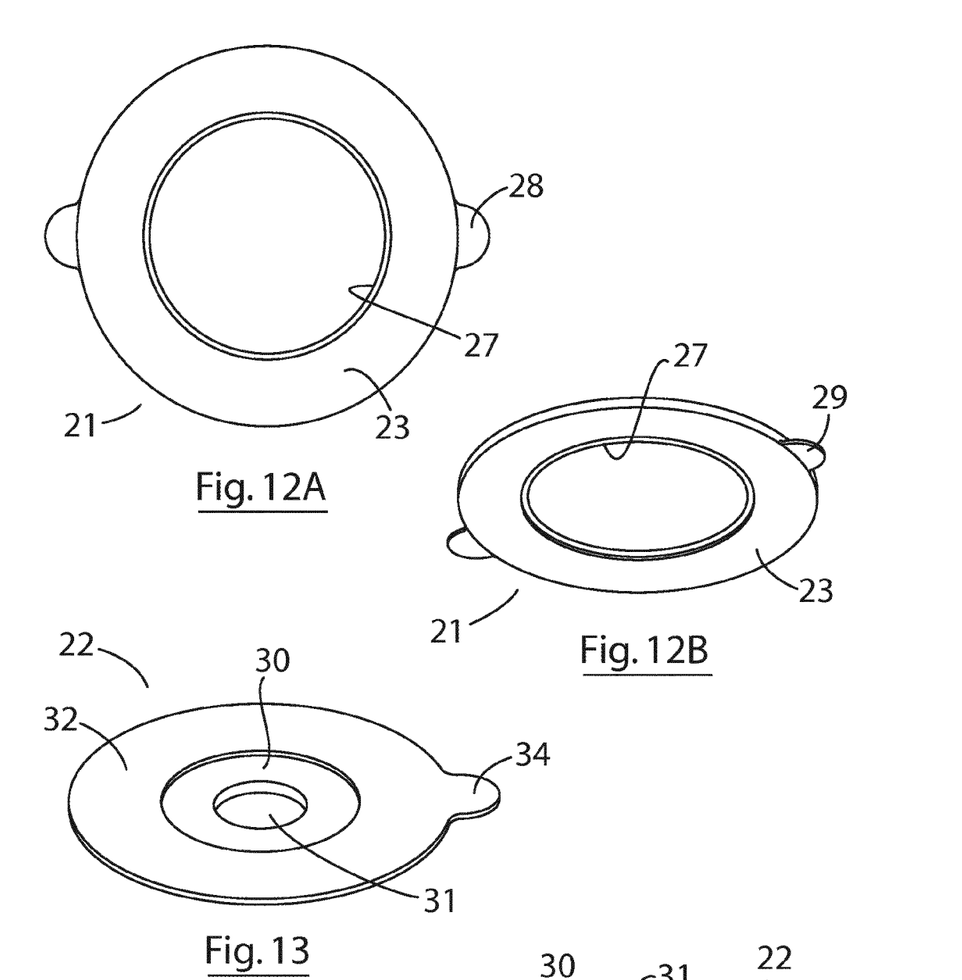
FIG. 12A is a bottom plan view of the reusable outer ring of FIG. 11
FIG. 12B is a perspective view from below the outer ring of FIG. 11.
FIG. 13 is a perspective view the inner ring forming the second part of the modular two-part fixing plate of the invention, showing the external (outward facing) side.

Referring specifically to FIGS. 11 and 12, the outer ring 21 has a skin abutting face 23 comprising silicone material for adhering safely to a users' skin, a protecting layer of polymer film 24 to which the silicone is cured for protecting the silicone material and for ease of handling, and an inner periphery comprising a stepped shoulder 25 for engagement with the inner ring 22. The inner circumference of the outer ring 21 comprises a hard plastic or silicone ring 27 which provides structure. Two tabs 28 are provided on the periphery of the outer ring to facilitate removal of the ring from the users' skin as well as facilitating positioning the ring on the users' skin.

Figure 14:
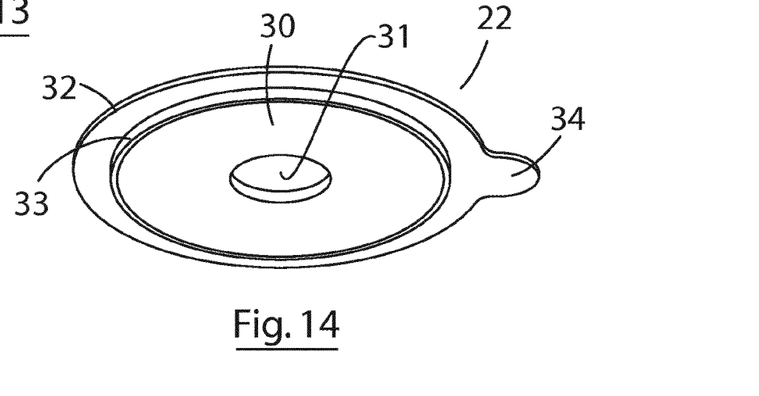
FIG. 14 is a perspective view of the inner ring of FIG. 13, showing the internal (skin facing) side.

Referring specifically to FIGS. 13 to 14, the inner ring 22 comprises a central annulus 30 formed of a mouldable hydrocolloid material having a central aperture 31 for receipt of a stoma, and a peripheral annular housing 32 which sits on top of the central annulus and has a circumferential periphery that extends beyond circumferential periphery of the central annulus, forming a shoulder 33 that is dimensioned for removable engagement with the stepped shoulder 25 of the outer ring 21. As illustrated in FIG. 14, when the inner and outer rings engage, the bottom face of the hydrocolloid annulus 30 is substantially flush with the silicone skin-abutting face 23 of the outer ring 21. The annular housing is formed of polyurethane material, and includes a single peripheral tab 34 to facilitate separation of the inner ring 22 and outer ring 21.

Figures 15A, 15B, 16A, 16B:
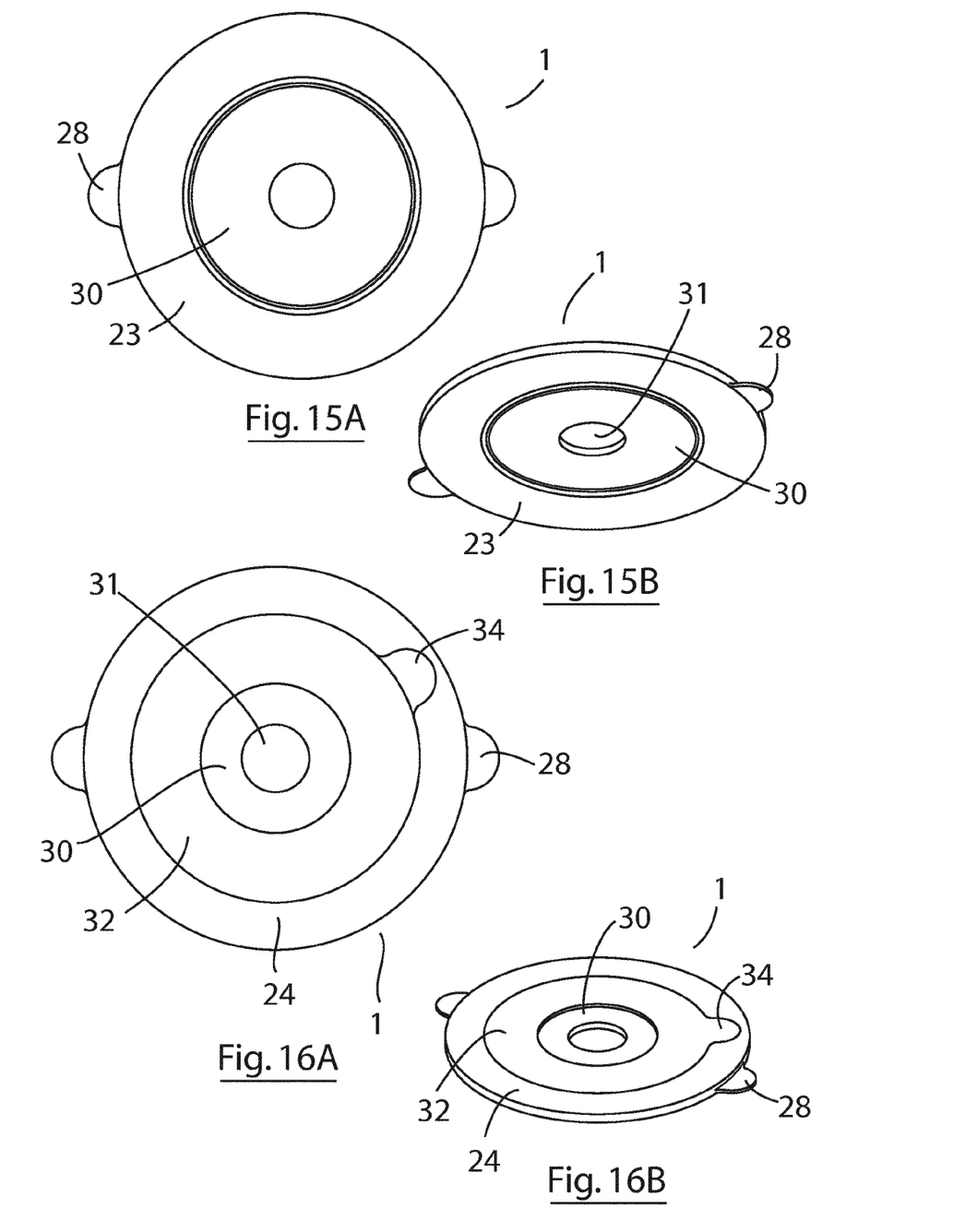
Figure 17A:
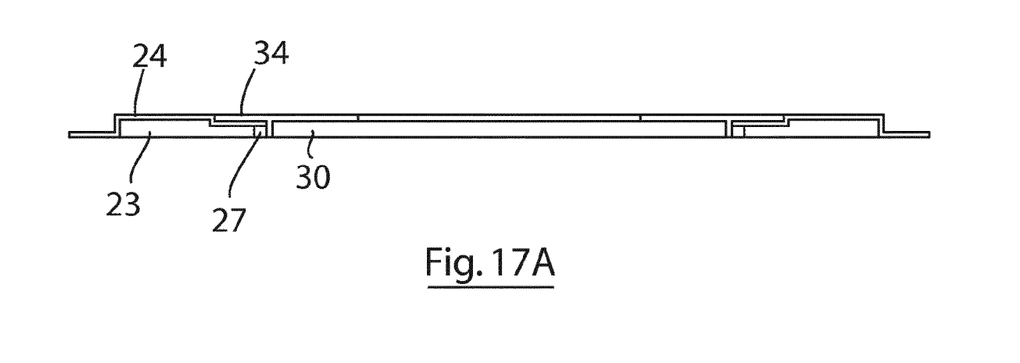
FIGS. 17A and 17B are sectional side elevational and perspective views of the modular two-part fixing plate of FIG. 16.
Figure 17B:
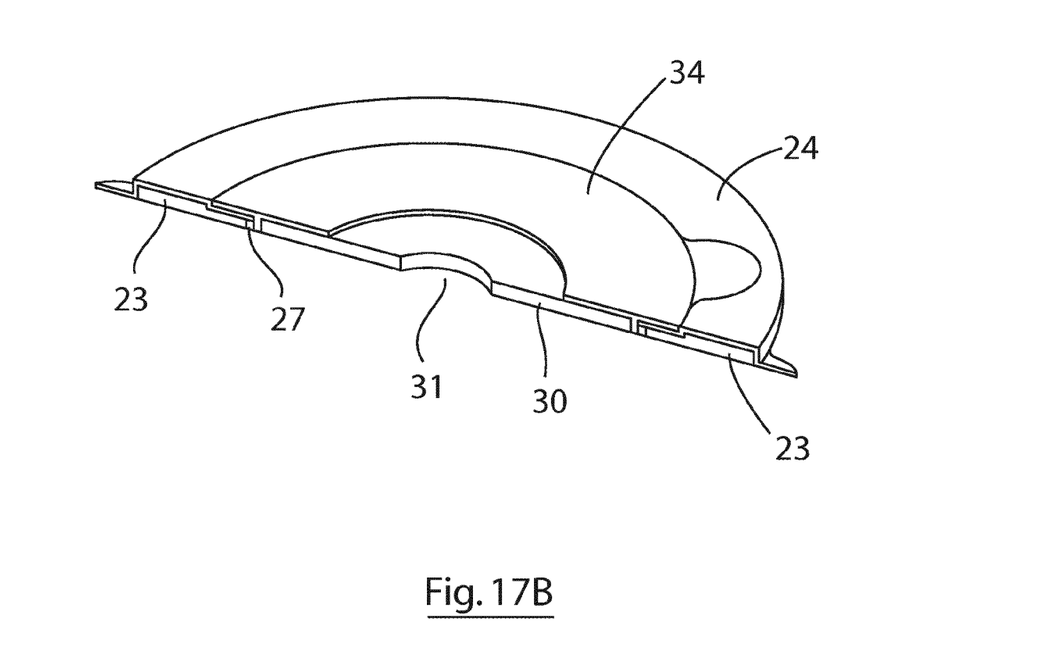

FIGS. 15 to 17 show the modular two-part fixing plate 1 in an assembled form, with the inner ring 22 engaged with the outer ring 21.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An ostomy attachment comprising a flexible annular seal configured to embrace a stoma and a spout that in use is disposed beneath the stoma and configured to collect ostomy output at skin level and direct ostomy output away from the patient and annular seal and into an ostomy bag, in which the flexible annular seal is formed from an absorbent material and the spout is formed from a non-absorbent material; wherein the spout comprises a partially annular inner rim portion configured to engage with a rim portion of the annular seal, in which the partially annular inner rim portion of the spout is flexible to allow it to conform to a non-uniform stoma.

2. An ostomy attachment as claimed in claim 1 in which the partially annular inner rim of the spout is thin and optionally angled to optimise collection of ostomy output and delivery of ostomy output directly into an ostomy bag.

3. An ostomy attachment as claimed in claim 1 in which the annular seal is an open ring comprising at least one mouldable arm that in use can be wrapped at least partially around the patients' stoma.

4. An ostomy attachment as claimed in claim 1 in which the annular seal comprises two mouldable arms configured for in-situ adjustment to fully embrace the patients' stoma.

5. An ostomy attachment as claimed in claim 1 in which the annular seal comprises a closed ring which is resiliently deformable.

6. An ostomy attachment as claimed in claim 1 in which the absorbent material is a hydrocolloid material.

7. An ostomy attachment as claimed in claim 1 in which the spout covers an external surface of a lower part of the annular seal.

8. An ostomy attachment as claimed in claim 1 in which an underside of the spout comprises a partially annular slot configured for engagement with a mouth of an ostomy bag.

9. An ostomy attachment as claimed in claim 1 in which the annular seal is flexible to allow it to conform to a non-uniform stoma.

10. An ostomy attachment as claimed in claim 1 in which the spout is detachably attached to the annular seal.

11. An ostomy attachment kit for assembling an ostomy attachment as claimed in claim 1, the kit comprising a plurality of flexible annular seals, each configured to embrace a stoma, and at least one spout configured for attachment to an internal rim of the seal and configured to direct ostomy output away from the patient and annular seal and into the ostomy bag during use.

12. An ostomy bag kit comprising an ostomy bag and an ostomy attachment according to claim 1.

13. A method for attaching an ostomy bag to a patient with a stoma, which method employs an ostomy bag having an aperture for receipt of ostomy output, and an ostomy attachment according to claim 1, the method comprising placing the ostomy attachment on the patient such that the flexible annular seal at least partially surrounds the patients' stoma and the spout is disposed below the patients' stoma, and attaching the ostomy bag to the ostomy attachment.

14. A method according to claim 13 in which the annular seal of the ostomy attachment is an open ring in which the open ring comprises at least one mouldable arm that in use can be wrapped at least partially around the patients' stoma, the method comprising the additional step of moulding the at least one mouldable arm around at least part of the patients' stoma.

15. A method according to claim 13 in which the annular seal comprises two mouldable arms configured for in-situ adjustment to fully embrace the patients' stoma, the method comprising the additional step of moulding the two mouldable arms around the patients' stoma.

16. A method according to claim 13 in which an underside of the spout comprises a partially annular slot configured for engagement with the ostomy bag, in which the step of attaching the bag to the ostomy attachment includes a step of engaging part of the bag with the slot on the underside of the spout.

* * * * *